United States Patent [19]

Kawano et al.

[11] Patent Number: 5,789,652
[45] Date of Patent: Aug. 4, 1998

[54] NON-INSULIN-DEPENDENT DIABETIC RAT

[75] Inventors: Kazuya Kawano, Tokushima-ken; Tsukasa Hirashima; Masao Kurosumi, both of Tokushima; Yuichi Saito, Tokushima-ken, all of Japan

[73] Assignee: Otsuka Pharmaceutical Co., Ltd., Tokyo-To, Japan

[21] Appl. No.: 568,408

[22] Filed: Dec. 6, 1995

Related U.S. Application Data

[63] Continuation of Ser. No. 809,432, Dec. 18, 1991, abandoned.

[30] Foreign Application Priority Data

Dec. 19, 1990 [JP] Japan .................... 2-419277
Feb. 14, 1991 [JP] Japan .................... 3-106956

[51] Int. Cl.$^6$ .................... C12N 5/00; C12N 15/00; A61K 49/00
[52] U.S. Cl. .................... 800/2; 424/9.2; 800/DIG. 4; 800/DIG. 5
[58] Field of Search .................... 800/2, DIG. 4, 800/DIG. 5; 424/9.2

[56] References Cited

PUBLICATIONS

Goto et al., *J. Japan Diab. Soc.*, 34(11):939–941(1991).
Mori et al., *J. Japan Diab. Soc.*, 31(12):909–915 (1988) (Abstract).
Kummelstiel, et al, *Am. J. Path.*, vol. XII, 83–97.
Kawano et al, *Rat Newsletter*, 22:14 (1989).
Bender et al, *Biochem. Genet.*, 24:1–11 (1985).
Adams et al, *Biochem. Genet.*, 22:611–629 (1984).
Yamada et al, *Japan J. Genet.*, 56:447–455 (1981).
Womack, *J. Hered.*, 63:41–42 (1972).
Womack, *Biochem. Genet.*, 9:13–24 (1973).
Matsumoto et al, *Biochem. Genet.*, 17:1121–1129 (1979).
Nikaido et al, *J. Hered.*, 75:419–420 (1984).
Katoh et al, *Lab. Anim.*, 20:158–161 (1986).
Hedrich et al, *Biochem. Genet.*, 25:79–93 (1987).
Womack, *Experimentia*, 28:1372 (1972).
Gasser et al, *Biochem. Genet.*, 10:207–217 (1973).
Mizuno et al, *Japan J. Genet.*, 53:137–142 (1978).
Bender et al, *Transplant. Proc.*, 11:1653–1656 (1979).
Bender et al, *Biochem. Genet.*, 20:221–228 (1982).
Matsumoto, *Biochem. Genet.*, 18:879–887 (1980).
Moutier et al, *Biochem. Genet.*, 8:321–328 (1973).
Moutier et al, *Biochem. Genet.*, 9:109–115 (1973).
Carleer et al, *Int. J. Biochem.*, 7:565–566 (1976).
Cramer et al, *Biochem. Genet.*, 23:623–629 (1985).
Ericksson et al, *Heredity*, 37:341–349 (1976).
Cramer et al, *Biochem. Genet.*, 24:217–227 (1986).
Brdicka et al, *Folia Biologica (Plaque,* 11:328–329 (1965).
Cramer, *Immunogenet.*, 13:555–558 (1981).
Carter, *Nature*, 224:1214 (1969).
Gasser, *Biochem. Genet.*, 6:61–63 (1972).
Coleman et al., *Diabetologia*, 9:287–293 (1973).
Coleman et al, *Diabetologia*, 10:607–610 (1974).
Makino et al, *Exp., Anim.*, 29(1):1–13 (1980).
Ikeda et al, *Diabetes*, 30:1045–1050 (1981).
Jackson et al, *Diabetes*, 30:887–889 (1981).
Lee et al, *Diabetes*, 30:106–111 (1981).
Lee, *Diabetologia*, 22:349–353 (1982).
Chappel, *Metabolism*, 32(7):8–10 (1983).
Elder et al, *J. Immunol.*, 130(4): 1723–1731 (1983).
Harada et al, *Diabetologia*, 27:604–606 (1984).
Funakawa et al, *Biomed. Res.*, 5(3):291–294 (1984).
Nakayama et al, *Japan. J. Vet. Sci.*, 48(1):149–153 (1986).
Woda et al, *J. Immunol.*, 136(3):856–859 (1986).
Terazono et al, *J. Biol. Chem.*, 263(5):2111–2114 (1988).
Wakisaka et al, *Diabetologia*, 31:291–296 (1988).
Teitelman et al, *Cell.*, 52:97–105 (1988).
Charlton et al, *Diabetes*, 38:441–447 (1989).
Kawano et al, *J. Gastrolenterol. Hepatl.*, 6:377–382 (1991).
Kawano et al, *Diabetes*, 40:1375–1381 (1991).
Tago et al, *J. Comp. Path.*, 104(4):367–377 (1991).
Kawano K. et al, "The LEC Rat: A New Model for Hepatitis and Liver Cancer" by Springer–Verlag Tokyo, pp. 30–40, 298–304 (1991).
Kawano et al, *Rat Newsletter*, 25:24–26 (1991).
Tago et al (1991) J. Comp. Path. 104, 367–377.
Velasquez et al (1989) Diabetes 38, 679–685.
Folgia et al (1950) Arch. Path. 150, 75–83.
Tsuchitani et al (1985) Lab. Animals 19, 200–207.
Goto (1975) Proced. Japan. Acad. 51, 80–85.

*Primary Examiner*—Deborah Crouch
*Attorney, Agent, or Firm*—Sughrue, Mion, Zinn, Macpeak & Seas, PLLC

[57] ABSTRACT

This invention relates to a non-insulin-dependent diabetic disease model rat derived and established from Long-Evans rats, more particularly, a non-insulin-dependent diabetic rat having specific biochemical gene markers in organs, plasma and red blood cells, with erythrocytes and B lymphocytes having specific major histocompatibility antigen markers, showing increases in plasma glucose and insulin levels on oral glucose loading and increases in urinary protein level with aging, with diabetic nephropathy manifested by nodular and diffuse lesions of the glomerulus of the kidney accompanying in individuals with glycosuria.

4 Claims, 3 Drawing Sheets

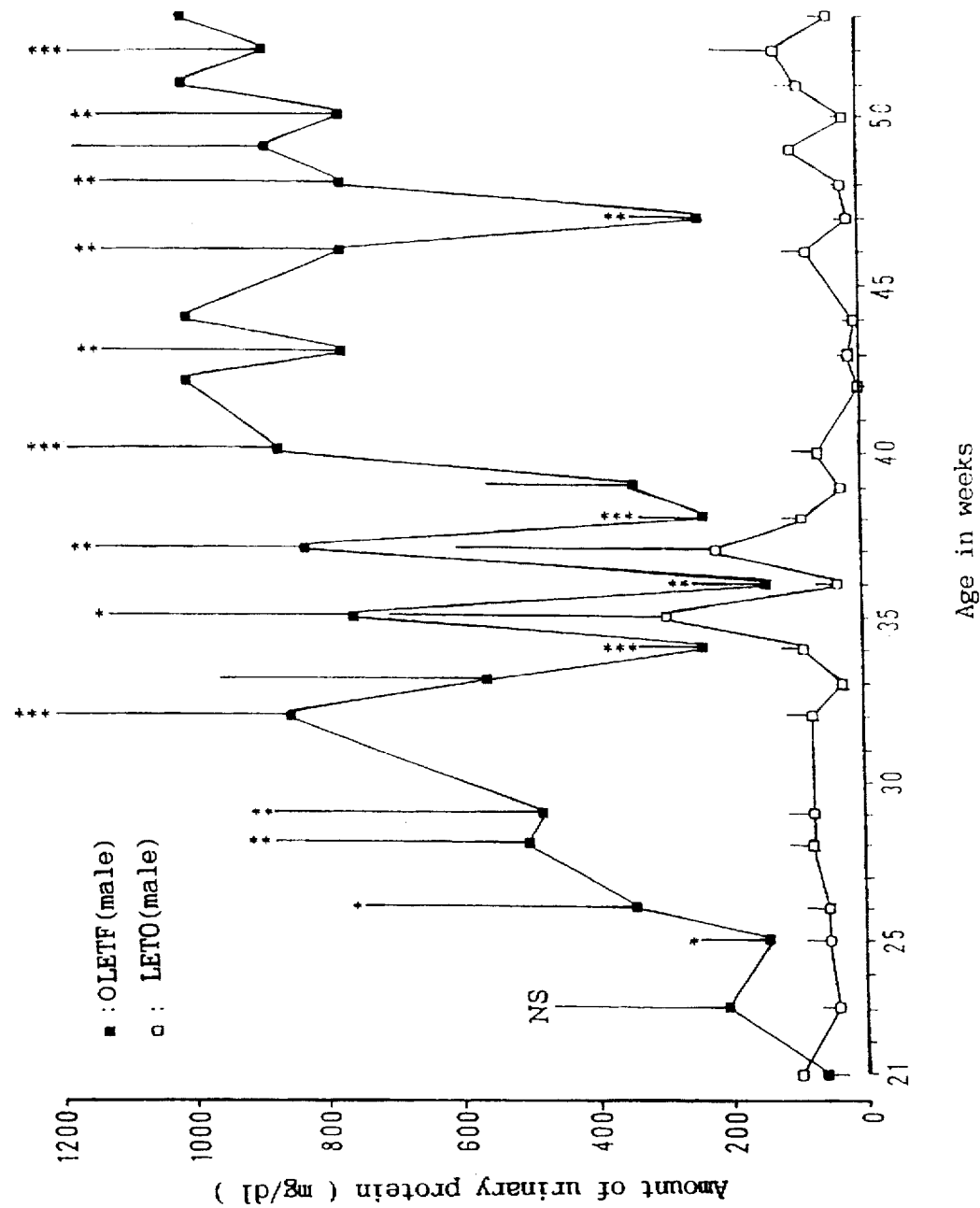

NON-INSULIN-DEPENDENT DIABETIC RAT

This is a Continuation of application Ser. No. 07/809,432, filed on Dec. 18, 1991 now abandoned.

The present invention relates to a novel non-insulin-dependent diabetic rat and, more particularly, to a disease model rat for non-insulin-dependent diabetes mellitus as established from Long-Evans rats by sib mating (brother-sister mating).

According to a WHO disease type classification, diabetes mellitus is classified into insulin-dependent diabetes mellitus (IDDM), symptoms of which appear acutely or sub-acutely owing to deficiency in the absolute quantity of insulin and which requires insulin therapy, and non-insulin-dependent diabetes mellitus (NIDDM), which features a slow progression of the disease and does not necessarily require insulin therapy.

As factors causing diabetes mellitus, there may be mentioned, among others, (1) a decreased absolute quantity of insulin, (2) a decreased efficiency of action of insulin in target organs, and (3) the presence of an anti-insulin substance [Tomio Tanese and Masakazu Abe: "Tonyobyo—Kiso to Rinsho (Diabetes mellitus—Fundamentals and Clinical Practice)", edited by Kinori Kosaka, Seiichiro Tarui and Takehiko Ide, published by Asakura Shoten, Tokyo, 1975, page 251]. However, the onset of diabetes mellitus is associated with a tangle of genetic factors and environmental factors and much remains unknown in many respects.

Furthermore, diabetes mellitus requires long-term therapy, and diabetes mellitus results in severe complications, such as diabetic cataract and diabetic nephropathy, which may become grave problems.

In order to study such diabetes mellitus, a diabetic state is produced in experimental animals by administration of streptozotocin or alloxan, for instance, and the animals are used for the investigation of the pathogenesis of diabetes or screening of therapeutic agents for diabetes. However, drug poisoning rarely causes diabetes mellitus and, accordingly, it is doubtful whether the use of the experimental animals mentioned above is valid or not. For this reason, it is desirable that animal model in which the onset of diabetes is close to that in humans be used to study diabetes mellitus. Such model animals known in the art include, for instance, BB rats [cf. Kansen, Men'eki, Ensho (Infection, Immunity, Inflammation), 15 (1), 28–29, 1985] and LETL rats [K. Kawano, T. Hirashima, S. Mori, F. Abe, M. Kurosumi and Y. Saitoh, A new strain of rat with insulin-dependent diabetes mellitus 'LETL rat', Rat News Letter, No. 22, Dec., 14–15 (1989)] for IDDM and, for NIDDM, GK rats [Goto, Y., Kakizaki, M. and Masaki, N., Spontaneous diabetes produced by selective breeding of normal Wistar rats, Proc. Jpn. Acad., 51, 80–85, 1975] and WBN/kob rats [M. Tsuchitani, T. Saegusa, I. Narama, T. Nishikawa and T. Gonda, A new diabetic strain of rat (WBN/kob), Laboratory Animals, 19, 200–207 (1985)], for instance.

However, the above-mentioned animal model for NIDDM do not show distinct diabetic complications. The advent of animal model for NIDDM with diabetic complications, which could replace the above-mentioned ones, is thus desired.

It is an object of the invention to establish a strain of rats capable of offering a model for non-insulin-dependent diabetes mellitus with complications such as diabetic nephropathy.

Another object of the invention is to establish a strain of rats capable of offering a model of the above-mentioned non-insulin-dependent diabetes mellitus and therefore useful for the screening of antidiabetic drugs and the elucidation of the pathology of non-insulin-dependent diabetes mellitus and of complications such as diabetic nephropathy, amongst others.

The above objects can be accomplished by rats offering a model of non-insulin-dependent diabetes mellitus and belonging to a strain derived and established from Long-Evans rats.

The present inventors have now established a novel strain of rats serving as model rats for non-insulin-dependent diabetes mellitus and have completed the present invention by mating male rats showing abnormal glucose tolerance with females of the same litter and repeating sib mating using offsprings thereof while employing the direct testing system ["Shin Jikken Dobutsu Gaku (New Textbook of Experimental Animals)", Kazuyoshi Maejima, Kozaburo Esaki, Motoo Shinoda, Chuhei Yamauchi, Tomotari Mitsuoka, Shigeru Sugano, Shigekatsu Tsuji and Kunio Doi (coauthors), Asakura Shoten, Tokyo, 1986, page 35] with results of an oral glucose tolerance test and the presence or absence of glycosuria used as indexes.

The Long-Evans strain-derived non-insulin-dependent diabetic rats of this invention are characterized by their having the following biochemical gene locus types:

| Biochemical gene locus | Type |
| --- | --- |
| Testicle acid phosphatase 2 | a |
| Testicle esterase 6 | a |
| Lung esterase 7 | b |
| Testicle esterase 8 | a |
| Testicle esterase 9 | c |
| Testicle esterase 10 | b |
| Liver aldehyde dehydrogenase 2 | c |
| Liver aldehyde dehydrogenase c | a |
| Liver glycerophosphate dehydrogenase 1 | a |
| Liver hydroxy acid oxidase | a |
| Erythrocyte catalase 1 | b |
| Erythrocyte hemoglobin beta chain | b |
| Plasma esterase 1 | b |
| Plasma esterase 2 | d |
| Plasma esterase Si | a |
| Plasma group-specific component | b |
| Small intestine esterase 1 | b |
| Small intestine esterase 3 | c |
| Digestive tract mucosa urinary pepsinogen 1 | a |
| Kidney esterase 4 | b |
| Kidney fumarate hydrogenase 1 | b |
| Kidney phosphogluconate dehydrogenase | b |
| Seminal vesicle protein 1 | a |

The non-insulin-dependent diabetic rats of this invention are also characterized by their having the following rat major histocompatibility antigen (RT1) markers:

| Major histocompatibility antigen (RT1) | Type |
| --- | --- |
| Erythrocyte RT1 class I antigen | u |
| B lymphocyte RT1 class II antigen | u |

Furthermore, the non-insulin-dependent diabetic rats of this invention are clearly distinguished from known diabetic rats in that an oral glucose tolerance test reveals increases in plasma glucose and insulin levels and the urinary protein level increases with age and in that glycosuria is accompanied by diabetic nephropathy manifested as nodular and diffuse lesions of the glomerulus of the kidney.

The non-insulin-dependent diabetic rats of this invention which have the above-mentioned characteristic features have been given the strain name OLETF (Otsuka Long-Evans Tokushima Fatty) by the present inventors. Hereinafter, this designation shall be used in this specification as well.

The OLETF rats of this invention can serve as diabetic rat model showing diabetes close to non-insulin-dependent diabetes mellitus in humans. The incidence of such diabetes is constant. Therefore, they are very useful in studying the pathology of non-insulin-dependent diabetes mellitus in further detail and in screening therapeutic agents for diabetic nephropathy, for instance.

The method of producing (breeding) the non-insulin-dependent diabetic rats of this invention comprises serial selective mating (sib mating) using, as ancestors, outbred Long-Evans rats purchased from Charles River Canada.

In 1982, while breeding outbred Long-Evans rats received from Charles River Canada, the present inventors happened to discover, among them, rats showing spontaneous glycosuria, polyuria and polyphagia with mild obesity. The characteristics of these rats were as follows: Only males showed increased plasma glucose in the oral glucose tolerance test performed around 3 to 4 months after birth, in spite of insulin response to glucose stimulation. This condition gradually gained in severity with age and, at 6 to 7 months of age, the oral glucose tolerance test had already revealed changes in plasma glucose level which are characteristic of diabetes mellitus type (peak level>300 mg/dl; 2-hour level>200 mg/dl). After 10 months, glycosuria appeared in 20 to 30% of individuals, and some rats showed the IGT (impaired glucose tolerance) type response with either of the peak and 2-hour plasma glucose levels reaching the threshold for diabetes mellitus. Individuals with glycosuria showed polyphagia, polyuria and polydipsia with only slight decreases in body weight. Histopathologically, the pancreatic islets of these rats showed a proliferation of islet cells. After the onset of glycosuria with decreasing plasma insulin level, typical degeneration and atrophy of the pancreatic islets were observed and nodular and diffuse lesions of glomeruli were noted as complications.

The Long-Evans strain-derived non-insulin-dependent diabetic rats mentioned above, whether male or female, show fertility when mated at the age of 9 to 10 weeks. After this period, however, the incidence of infertility in the female increases. Therefore, the present inventor conducted line breeding through two generations in accordance with the direct testing system ["Shin Jikken Dobutsugaku", Kazutoshi Maejima, Kozaburo Esaki, Motoo Shinoda, Chuhei Yamauchi, Tomotari Mitsuoka, Shigeru Sugano, Shigekatsu Tsuji and Kunio Doi (coauthors), published by Asakura Shoten, 1986, page 35] using the results of oral glucose tolerance tests and the appearance of glycosuria as indicators.

For breeding, rats were housed in cages (Econ TPX cages, Clea Japan) (one or two rats per cage) littered with Beta-Chip (Northeastern Products, U.S.A.) and fed in an SPF (specific pathogen-free) environment ["Shin Jikken Dobutsugaku", Kazutoshi Maejima, Kozaburo Esaki, Motoo Shinoda, Chuhei Yamauchi, Tomotari Mitsuoka, Shigeru Sugano, Shigekatsu Tsuji and Kunio Doi Asakura Shoten, 1986, page 104] where the conditions were controlled as follows: temperature 23°±2° C., humidity 55±5%, and lighting from 7:00 a.m. to 7:00 p.m. The animals received a laboratory diet (CRF-1, Oriental Yeast Co.) and ordinary tap water ad libitum.

For detecting the onset of diabetes mellitus during the breeding period, an oral glucose tolerance test was performed at and after 25 weeks of age and urinary glucose monitoring was carried out using a urine testing paper (Uri-sticks, Miles-Sankyo) with a frequency of 1 or 2 times in a month. It is to be noted that the breeder may, in the course of routine breeding management, notice the onset of diabetes mellitus from increased urine volumes and the odor of chips wetted with glucose-containing urine.

Using the above breeding conditions and testing methods, the present inventors succeeded in creating the non-insulin-dependent diabetic disease model rats of this invention, which stably develop diabetes mellitus close to non-insulin-dependent diabetes mellitus in humans, by mating those Long-Evans rats manifesting non-insulin-dependent diabetes mellitus for 20 generations. The cumulative incidences of diabetes mellitus and IGT were 86.0% (301/350) and 9.7% (34/350), respectively, in male OLETF rats after the 20th generation.

The non-insulin-dependent diabetic rats provided by the present invention are useful as animal models for the clarification of the pathology of non-insulin-dependent mellitus, the study of diabetic nephropathy, and the screening of antidiabetic agents, for instance.

The following examples are further illustrative of the invention. They are, however, by no means limiting on the scope of the invention.

The accompanying drawings are referred to in the examples.

FIG. 3 is a graph showing the change with aging in urinary protein in the OLETF rat of the invention according to Example 4 of the invention.

EXAMPLE 1

Figure 1:
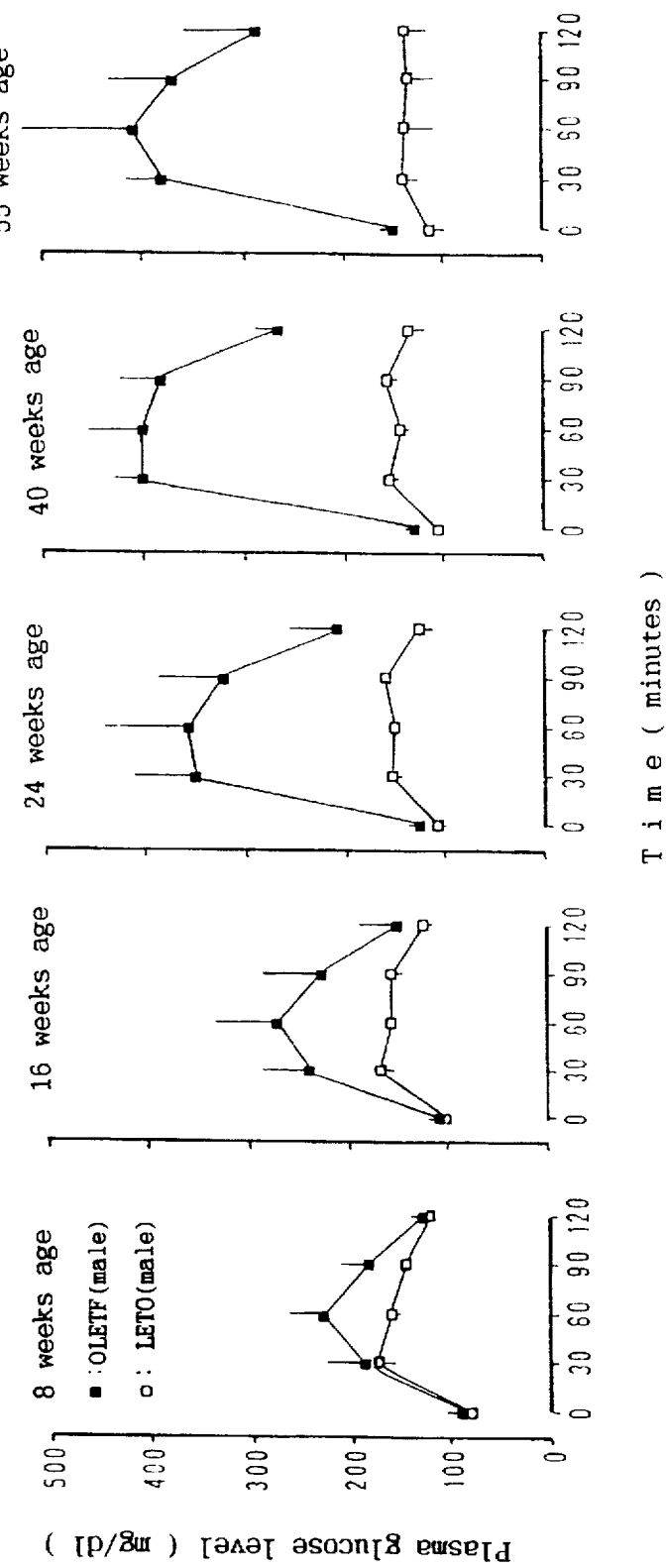
FIG. 1 is a graph showing the change with aging in plasma glucose in the OLETF rat of the invention as found in the oral glucose loading test according to Example 2-2) of the invention.

Mating of rats (1) Breeding of rats

Long-Evans rats were purchased from Charles River Canada. Beta-Chip (Northeastern Products, U.S.A.) was placed in cages (Econ TPX cages, Clea Japan) for bedding. One or two animals were housed in each cage. Breeding was conducted in an SPF environment where the temperature was controlled at 23°±2° C., the humidity at 55±5%, and the lighting hours from 7 a.m. to 7 p.m. The animals were given a laboratory diet (CRF-1, Oriental Yeast) and ordinary tap water ad libitum.

(2) Testing for diabetes mellitus during breeding

For detecting the onset of diabetes mellitus during breeding, rats urine samples were tested with a urine testing paper (Uri-sticks, Miles-Sankyo) once or twice in a month. It is to be noted that, during ordinary breeding management, the onset of diabetes mellitus can also be perceived from increased urine volumes, wetting of chips with glucose-containing urine and the characteristic odor of diabetes mellitus even prior to the above tests.

(3) Mating of rats a: Establishment of the OLETF diabetic rat of the invention

The rats purchased and the rats of each of the subsequent generations were numbered serially.

Mating of No. 36 female rat with No. 42 male rat (not manifesting NIDDM), which was an offspring of other parents, resulted in the birth of 15 rats (9 males and 7 females, No. 30 to No. 44). In 8 of the male rats, NIDDM was manifested. This generation was designated as generation zero (F0) of the OLETF rat strain of this invention.

Then, among the above-mentioned F0 sibmates, No. 39 female was mated with No. 32 male (manifesting NIDDM)

to give 10 first generation (F1) rats (4 males and 6 females, No. 1 to No. 10). In 4 of the males, the onset of NIDDM was observed.

Sib mating of No. 5 F1 female with No. 1 F1 male (manifesting NIDDM) gave 9 F2 rats (4 males, 5 females, No. 11 to No. 19). Two out of the 4 males showed NIDDM.

Mating of No. 17 F2 female with No. 13 F2 male (manifesting NIDDM) gave F3 rats.

Mating of No. 25 F3 female with No. 23 F3 male (manifesting NIDDM) gave F4 rats.

Mating of No. 4 F4 female with No. 1 F4 male (manifesting NIDDM) gave F5 rats.

Mating of No. 58 F5 female with No. 54 F5 male (manifesting NIDDM) gave F6 rats.

Mating of No. 52 F6 female with No. 45 F6 male (manifesting NIDDM) gave F7 rats.

Mating of No. 18 F7 female with No. 14 F7 male (not manifesting NIDDM) gave F8 rats.

Mating of 64 F8 female with No. 62 F8 male (not manifesting NIDDM) gave F9 rats.

Mating of No. 69 F9 female with No. 62 F9 male (manifesting NIDDM) gave F10 rats.

Mating of No. 124 F10 female with No. 120 F10 male (manifesting NIDDM) gave F11 rats.

Mating of No. 104 F11 female with No. 98 F11 male (manifesting NIDDM) gave F12 rats.

Mating of No. 55 F12 female with No. 50 F12 male (manifesting NIDDM) gave F13 rats.

Mating of No. 84 F13 female with No. 81 F13 male (manifesting NIDDM) gave F14 rats.

Mating of No. 60 F14 female with No. 61 F14 male (manifesting NIDDM) gave F15 rats.

Mating of No.96 F15 female with No. 88 F15 male (not manifesting NIDDM) gave F16 rats.

Mating of No. 119 F16 female with No. 112 F16 male (manifesting NIDDM) gave F17 rats.

Mating of No. 611 F17 female with No. 603 F17 male (not manifesting NIDDM) gave F18 rats.

Mating of No. 608 F18 female with No. 602 F18 male (not manifesting NIDDM) gave F19 rats.

Mating of No. 615 F19 female with No. 612 F19 male (not manifesting NIDDM) gave F20 rats.

Thus, after 20 generations, the OLETF rat strain of this invention was established as an inbred line. The inventors have maintained and bred the non-insulin-dependent diabetic disease model rat (OLETF) strain ever since the 20th generation (F20).

The OLETF rat strain of this invention as established in the above manner has been maintained by line breeding in Otsuka Pharmaceutical Co., Ltd. and rats of said strain are always available therefrom. Fertilized embryos from rats of said OLETF strain have been frozen and stored at said company.

b: Establishment of a control strain of rats (LETO strain).

A rat strain named LETO (Long-Evans Tokushima Otsuka) was established as a control strain from the same colony of rats used for the establishment of the above-mentioned OLETF strain.

First, No. 50 female rat was mated with No. 45 male rat (not manifesting NIDDM) to give 11 offspring rats. These were regarded as generation zero (F0) of the control strain LETO. Mating was started from the establishment of said control strain of rats not manifesting non-insulin-dependent diabetes mellitus, as follows:

Among the F0 sibmates, No. 55 female was mated with No. 48 male (not manifesting NIDDM) to give 5 F1 rats (not manifesting NIDDM).

Sib mating between No. 68 F1 female with No. 65 F1 male (not manifesting NIDDM) gave F2 rats.

No. 49 F2 female was mated with No. 47 F2 male (not manifesting NIDDM) to give F3 rats.

No. 66 F3 female was mated with No. 59 F3 male (not manifesting NIDDM) to give F4 rats.

No. 150 F4 female was mated with No. 148 F4 male (not manifesting NIDDM) to give F5 rats.

No. 193 F5 female was mated with No. 190 F5 male (not manifesting NIDDM) to give F6 rats.

No. 111 F6 female was mated with No. 106 F6 male (not manifesting NIDDM) to give F7 rats.

No. 142 F7 female was mated with No. 135 F7 male (not manifesting NIDDM) to give F8 rats.

No. 118 F8 female was mated with No. 114 F8 male (not manifesting NIDDM) to give F9 rats.

No. 94 F9 female was mated with No. 93 F9 male (not manifesting NIDDM) to give F10 rats.

No. 147 F10 female was mated with No. 143 F10 male (not manifesting NIDDM) to give F11 rats.

No. 150 F11 female was mated with No. 147 F11 male (not manifesting NIDDM) to give F12 rats.

No. 183 F12 female was mated with No. 179 F12 male (not manifesting NIDDM) to give F13 rats.

None of the rats born by sib mating carried out as described above manifested NIDDM.

No. 166 F13 female was mated with No. 162 F13 male (not manifesting NIDDM) to give F14(1) rats.

No. 286 F14(1) female was mated with No. 283 F14(1) male (not manifesting NIDDM) to give F15(1) rats.

No. 306 F15(1) female was mated with No. 301 F15(1) male (not manifesting NIDDM) to give F16(1) rats.

No. 630 F16(1) female was mated with No. 626 F16(1) male (not manifesting NIDDM) to give F17(1) rats.

No. 613 F17(1) female was mated with No. 609 F17(1) male (not manifesting NIDDM) to give F18(1) rats.

No. 618 F18(1) female was mated with No. 614 F18(1) male (not manifesting NIDDM) to give F19(1) rats.

Mating of No. 606 F19(1) female with No. 601 F19(1) male (not manifesting NIDDM) gave F20(1) rats.

The LETO rat stain has thus been established. This strain has been maintained by the present inventors, showing stable growth without manifestion of NIDDM.

EXAMPLE 2

Test for diabetes mellitus

1) Oral glucose tolerance test (OGTT)

Glucose (Wako Pure Chemical Industries) was dissolved in tap water to a concentration of 50%. The solution was administered orally to rats fasted for 18 hours at a dose of 2 g of glucose per kg of body weight. Plasma glucose levels were determined before and 30 minutes, 60 minutes, 90 minutes and 120 minutes after administration, and plasma insulin (immunoreactive insulin, IRI) levels were determined before administration and 60 minutes and 120 minutes after administration. For the above determinations, blood samples were taken from the tail vein.

2) Determination of plasma glucose

Each blood sample obtained as described above under 1) was centrifuged at 3,000 rpm for 20 minutes and the supernatant was used as a sample for glucose level determination. The plasma glucose level determination was performed using Glucose B Test Wako (Wako Pure Chemical Industries).

3) Determination of plasma insulin

Using the rat plasma obtained in the same manner as described above under 2), plasma insulin level determination was performed with the aid of Incstar's rat insulin assay kit.

7

Insulin was determined by radioimmunoassay (RIA) as follows. To 0.05 ml of the sample obtained as described above were added 0.1 ml of guinea pig anti-insulin serum (contained in the above-mentioned kit) and 0.2 ml of borate buffer (0.1M, pH 8.5) containing 0.25% bovine serum albumin (BSA, Sigma), and the mixture was incubated at 4° C. for 24 hours. Then, 0.1 ml of $^{125}I$ porcine insulin solution (contained in the above-mentioned kit; two-fold diluted with BSA borate buffer) was added and the mixture was incubated at 4° C. for 72 hours. Rabbit anti-guinea pig antiserum (0.5 ml) was added to the reaction mixture and the resultant mixture was allowed to stand at room temperature for 25 minutes, followed by 30 minutes of centrifugation at 4° C. and 3,000 rpm. The supernatant was removed by decantation. Both the bound reaction product and the non-bound portion were measured for radioactivity for 2 minutes (using an Aloka ARC N5384 counter). The plasma insulin level was calculated using a standard curve prepared simultaneously.

Figure 2:
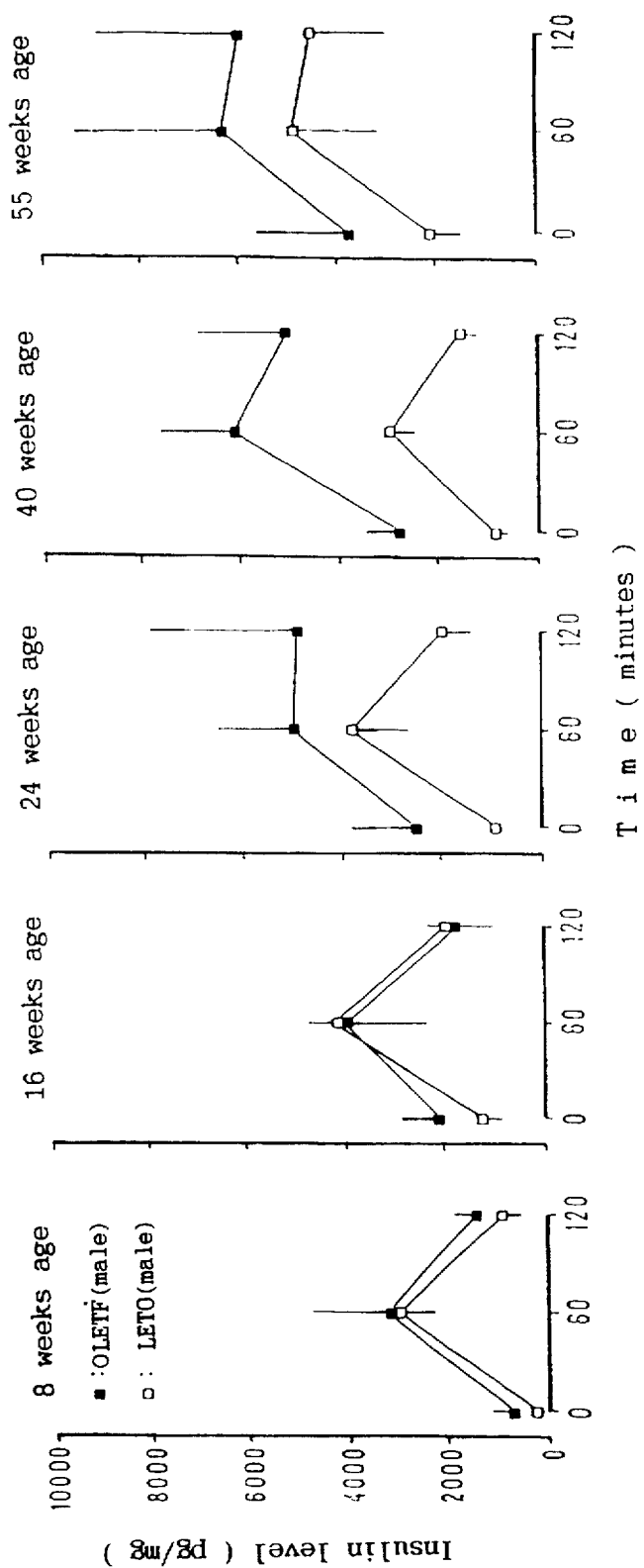
FIG. 2 is a graph showing the change with aging in plasma insulin level in the OLETF rat of the invention as found in the oral glucose loading test according to Example 2-3) of the invention.

The change of the plasma glucose level with aging as revealed by the above-mentioned oral glucose tolerance test is shown in FIG. 1. The change of the plasma insulin level with aging is shown in FIG. 2.

In each figure, the abscissa is for the time (in minutes) and the ordinate for the plasma glucose level (mg/dl) or insulin level (pg/ml), respectively. Each data is shown in terms of means ± standard deviation.

As is evident from FIG. 1, the plasma glucose level in OLETF rats is already significantly higher at the age of 8 weeks than that in normal (LETO) rats when compared in terms of the values obtained 60 minutes and 90 minutes after glucose loading. The increase in plasma glucose level in OLETF rats became gradually more remarkable and, at the age of 24 weeks, showed a diabetic type. At 40 weeks and 55 weeks of age, the peak value was 400 mg/dl or more.

On the other hand, the insulin level in OLETF rats was significantly higher than that in LETO rats at 8 weeks and 16 weeks of age when compared in terms of the value before loading, but showed no significant difference from that in LETO rats when compared in terms of the 60-minute and 120-minute levels, with great variations among individuals. At ages over 24 weeks after birth, the insulin value was at a clearly high level. This tendency was more prominent at 40 weeks and 50 weeks of age.

When rats developed glycosuria, their plasma glucose levels increased, whereas their insulin levels decreased.

The plasma glucose and insulin levels in LETO rats following glucose loading remained within the respective normal ranges.

EXAMPLE 3
Determination of urinary protein

The urinary protein was determined using Ames test paper (Miles-Sankyo). The rat urine was applied to the test paper and calorimetrically graded according to a six-grade schedule (negative: 0 mg/dl, ±: 0 mg/dl, +: 30 mg/dl, ++: 100 mg/dl, +++: 300 mg/dl, ++++: 1000 mg/dl) to estimate the amount of urinary protein. The change in the amount of urinary protein with aging is shown in FIG. 3.

In FIG. 3, the abscissa represents age in weeks and the ordinate represents the amount of urinary protein (mg/dl). The amount of urinary protein (mg/dl) is expressed in mean ± standard deviation, and the symbols *,  and * for data at each age stands for $p<0.05$, $p<0.01$ and $p<0.001$, respectively.

It is apparent from FIG. 3 that compared with normal rats (LETO), the urinary protein in OLETF rats began to increase markedly around 25 weeks of age.

8

EXAMPLE 4
Determination of biochemical gene locus types (1) Typing of acid phosphatase-2 (Acp-2)

Typing of testicular Acp-2 was carried out by the method of Bender et al. [Bender, K., Bissbort, S. Kuhn, A., Nagel, M. and Gunther, E., Biochem. Genet., 24, 1–11, (1985)].

Thus, 0.5 g of testis was homogenized with 1 ml of distilled water (using a Polytron homogenizer) and the homogenate was centrifuged at 13000 rpm (4° C.) for 10 minutes. The supernatant was taken and used.

The above sample was applied, in a portion of 0.6 µl, to a cellulose acetate membrane (Titan III-LIPO, Helena) and using Tris-histidine buffer (pH 5.9), electrophoresis in the direction of + to − at 4° C. and 120 V for 60 minutes.

After electrophoresis, the cellulose acetate membrane was immersed in the following dye bath at 37° C. for 1 hour and fixed with 5% acetic acid. Based on the migration pattern, the type of Acp-2 in the sample was determined in accordance with the literature referred to above.

[Dye bath composition]

α- or β-Naphthyl phosphate 10 mg

Fast violet B salt 10 mg

1M Citrate buffer (pH 4.5) 50 µl

Distilled water (DW) To make 10 ml (2) and (3) Typing of aldehyde dehydrogenase-2 (Ahd-2) and aldehyde dehydrogenase-c (Ahd-c)

Typing of liver Ahd-2 and Ahd-c was performed in accordance with the method of Adams [Adams, M., Baverstock, P. R., Watts, C. H. S., and Gutman, G. A., Biochem. Genet., 22, 611–629 (1984)]. Thus, 0.5 g of liver was homogenized with 1 ml of distilled water (using a Polytron homogenizer) and the homogenate was centrifuged at 13000 rpm (4° C.) for 10 minutes. The supernatant was taken and used.

The above sample was applied, in a portion of 0.3 µl, to a cellulose acetate membrane (Titan III-Lipo, Helena) and using Tris-glycine buffer (pH 8.6), electrophoresis in the direction of − to + was performed at 4° C. and 200 V for 30 minutes.

Following electrophoresis, the cellulose acetate membrane was stained (37° C., 1 hour) using the dye bath described below and fixed with 5% acetic acid. Then, based on the migration pattern, the types of Ahd-2 and Ahd-c in the above sample were determined in accordance with the literature referred to above.

[Dye bath composition]

1M Tris-HCl (pH 8.0) 0.1 ml

Acetaldehyde 0.5 ml

NAD (nicotinamide adenine dinucleotide) 12.5 mg

1M KCl 1 ml

Sodium pyruvate 25 mg

Pyrazole 25 mg

MTT (3-(4,5-dimethylthiazolyl-2)-2,5-diphenyltetrazolium bromide) 3 mg

PMS (phenazine methosulfate) 1 mg

DW To make 10 ml (4) Typing of erythrocyte catalase-1 (Cs-1)

A rat was laparotomized under ether anesthesia and the blood was drawn from the abdominal inferior vena cava. The collected blood was centrifuged at 3000 rpm (4° C.) for 10 minutes and the erythrocytes were washed by adding 5 ml of 0.8% NaCl solution. This washing procedure was performed twice, followed by centrifuging under the above conditions to provide an erythrocyte pack (RBC pack). To one volume of this RBC pack was added one volume of water for hemolysis and the mixture was centrifuged at 13000 rpm (4° C.) for 10 minutes. Then, using the supernatant, typing of Cs-1 was performed in accordance with the method of Yamada et al. [Yamada, J., Nikaido, H. and Kondo, Y., Jpn. J. Genet., 56, 447–455 (1981)].

The above sample was diluted 100–200-fold with 0.015M Tris-HCl buffer (pH 8.8) and applied, in a portion of 0.6 μl, to a cellulose acetate membrane (Titan III-Lipo, Helena). Then, using Tris-boric acid buffer (pH 8.6) containing 0.02M EDTA, electrophoresis in the direction of − to + was then performed at 200 V for 30 minutes.

After electrophoresis, the cellulose acetate membrane was washed with 1 mM hydrogen peroxide solution twice in one minute and further washed with water. The membrane was then immersed in a mixture of 5 ml of 0.05M ferric chloride and 5 ml of 0.05M potassium ferricyanide and the reaction is promptly quenched with 5% acetic acid. Based on the resulting migration pattern, the type of Cs-1 in the sample was determined in accordance with the literature referred to above.

(5), (6), (7), (8) and (9) Typing of plasma esterase-1 (Es-1), esterase-2 (Es-2) and esterase-Si (Es-Si) and of small intestine esterase-1 (Es-1) and esterase-3 (Es-3)

A rat was laparotomized under ether anesthesia and the blood was drawn from the abdominal inferior vena cava. The small intestine was also isolated. The collected blood was centrifuged at 3000 rpm (4° C.) for 10 minutes to separate the plasma.

The small intestine, 0.5 g, was homogenized with 1 ml of distilled water (using a Polytron homogenizer) and centrifuged at 13000 rpm (4° C.) for 10 minutes and the supernatant was taken and used as a sample.

The above sample was diluted 2-fold with the diluent IVA [25 ml of 0.5M Tris-HCl buffer (pH 6.8), 40 ml of glycerin, 20 ml of 0.01% BPB and 15 ml of water] and a 5 μl portion of the dilution was applied to 10% polyacrylamide gel [prepared from 5 ml of IA, 5 ml of IB, 1.25 ml of IIC, 0.5 ml of IID and 8.25 ml of DW (see below), total 20 ml]. Then, using Tris-glycine buffer (pH 8.6), electrophoresis in the direction of − to + was performed at 4° C. and 10 mA for 30 minutes and, then, at 15 mA for 30 minutes (for plasma esterase) or at 15 mA for 65 minutes (for small intestine esterase).

IA:
Polyacrylamide 39.0 g
Bis 1.0 g
Glycerin 20.0 ml
$H_2O$ To make 100.0 ml

IB:
Tris 9.15 g
Concentrated HCl ~3.0 ml
$H_2O$ To make 100.0 ml

IIC:
Ammonium persulfate 0.4 g
$H_2O$ To make 100.0 ml

IID:
TEMED 2.0 ml
$H_2O$ To make 100.0 ml

After electrophoresis, the esterase was stained using the dye bath described below and fixed with 5% acetic acid and the types of Es-1, Es-Si and Es-3 in the above sample were determined from the migration distances in accordance with the literature listed below.

[Dye bath composition]

α- or β-Naphtyl butyrate 10 μl
Fast violet B salt 50 mg
Acetone 100 μl
1M Phosphate buffer (pH 6.8) 100 μl
DW To make 10 ml

[The literature pertinent to types of Es-1, Es-2, Es-Si and Es-3]

Womack, J. E., J. Hered., 63, 41–42 (1972)
Womack, J. E., Biochem. Genet., 9, 13–24 (1973)
Matsumoto, K., Syuto, B., Miyake, Y-I., Matsuhashi, A. and Aizawa, M., Biochem. Genet., 17, 1121–1129 (1979)
Nikaido, H., Hayakawa, J., Kondo, Y., and Yamada, J., J. Hered., 75, 419–420 (1984)
Katoh, H., Shoji, Y., Yoshimura, Y., and Esaki, K., Lab. Anim., 20, 158–161 (1986)
Hedrich, H. J., von Deimling, O. and Kluge, R., Biochem. Genet., 25, 79–93 (1987)
Womack, J. E., Experientia, 28, 1372 (1972)
Gasser, D. L., Silvers, W. K., Reynolds, H. M. Jr., Black, G., and Palmm, J., Biochem. Genet., 10, 207–217 (1983)
Mizuno, M. and Suzuki, K., Jpn. Genet., 53, 137–142 (1978)

(10) Typing of renal esterase-4 (Es-4)

A rat was laparotomized under ether anesthesia and the kidneys were isolated. A 0.5 g portion of the kidney was homogenized with 1 ml of distilled water (using a Polytron homogenizer) and centrifuged at 13000 rpm (4° C.) for 10 minutes. The supernatant was taken and used as a sample. A 5 μl portion of this sample was applied to the same 10% polyacrylamide gel as used under (5)–(9) and using 0.0125M Tris-glycine buffer (pH 8.6), electrophoresis in the direction of − to + was performed at 4° C. and 15 mA for 65 minutes.

After electrophoresis, the esterase-4 was stained using the same dye bath as used under (5)–(9) and fixed with 5% acetic acid and the type of Es-4 in the sample was determined from the migration distance in accordance with the literature [Womack, J. E., Biochem. Genet., 9, 13–24 (1973)].

(11) Typing of testicular esterase-6 (Es-6)

The testes were isolated from a rat under ether anesthesia. A 0.5 g portion of the testes was homogenized with 1 ml of distilled water (using a Polytron homogenizer) and centrifuged at 13000 rpm (4° C.) for 10 minutes and the supernatant was taken and used as a sample. This sample was diluted two-fold with the diluent IVA and a 5 μl portion of the dilution was applied to 8% polyacrylamide gel [prepared from 4 ml of IA, 5 ml of IB, 1.25 ml of IIC, 0.5 ml of IID and 9.25 ml of DW, total 20 ml). Then, using 0.0125M Tris-glycine buffer (pH 8.6), electrophoresis in the direction of − to + was performed at 10 mA for 30 minutes and, then, at 15 mA for 30 minutes (4° C.). After electrophoresis, the esterase-6 was stained using the dye bath described below and fixed with 5% acetic acid and the type of Es-6 in the sample was determined from the migration distance in accordance with the literature [Bender, K., Nagel, M., Muller, C. R. and Gunther, E., Transplant. Proceed., 11, 1653–1656 (1979); Bender, K., Nagel, M. and Gunther, E., Biochem. Genet., 20, 221–228 (1982)].

[Dye bath composition]

1M Phosphate buffer (pH 6.8) 1 ml
Potassium ferricyanide 6 mg
Potassium ferrocyanide 8 mg
5-Bromoindoxylacetic acid (in DMSO) 8 mg
DW To make 10 ml

(12) Typing of lung esterase-7 (Es-7)

The lungs were excised from a rat under ether anesthesia and a 0.5 g portion of the lung tissue was homogenized with 1 ml of distilled water (using a Polytron homogenizer) and centrifuged at 13000 rpm (4° C.) for 10 minutes and the supernatant was taken and used as a sample. This sample was diluted two-fold with the diluent IVA and a 10 μl portion of the dilution was applied to the same 8% polyacrylamide gel as used under (11). Then, using 0.0125M Tris-glycine buffer (pH 8.6), electrophoresis in the direction of − to + was performed at 10 mA for 30 minutes and, then, at 15 mA for 30 minutes (4° C.). After electrophoresis, the esterase-7 was stained using the dye bath described below and fixed with 5% acetic acid and the type of Es-7 in the sample was determined from the migration distance in accordance with the literature [Matsumoto, K., Biochem. Genet., 18, 879–887 (1980)].

[Dye bath composition]

α- or β-Naphtyl butyrate 10 μl

Fast violet B salt 50 mg

Acetone 100 μl

1M Phosphate buffer (pH 6.8) 100 μl

DW To make 10 ml (13), (14) and (15) Typing of testicular esterase-8 (Es-8), esterase-9 (Es-9) and esterase-10 (Es-10)

The testes were isolated from a rat under ether anesthesia. A 0.5 g portion of the testes was homogenized with 1 ml of distilled water (using a Polytron homogenizer) and centrifuged at 13000 rpm (4° C.) for 10 minutes and the supernatant was taken and used as a sample. This sample was diluted two-fold with the diluent IVA and a 10 μl portion of the dilution was applied to the same 8% polyacrylamide gel as used under (11). Then, using 0.0125M Tris-glycine buffer (pH 8.6), electrophoresis in the direction of − to + was performed at 10 mA for 30 minutes and, then, at 15 mA for 30 minutes (4° C.). After electrophoresis, the esterases were stained using the dye bath described below and fixed with 5% acetic acid and the types of Es-8, Es-9 and Es-10 in the sample were determined from the migration distances in accordance with the literature listed below.

[Dye bath composition]

α- or β-Naphtyl butyrate 10 μl

Fast violet B salt 50 mg

Acetone 100 μl

1M Phosphate buffer (pH 6.8) 100 μl

DW To make 10 ml

[The literature pertinent to types of Es-8, Es-9 and Es-10]

Moutier, R., Toyama, K. and Charrier, M. F., Biochem. Genet., 8, 321–328 (1973)

Moutier, R., Toyama, K. and Charrier, M. F., Biochem. Genet., 9, 109–115 (1973)

Matsumoto, K., Biochem. Genet., 18, 879–887 (1980)

(16) Typing of renal fumarate hydrogenase (Fh-1)

A rat was laparotomized under ether anesthesia and the kidneys were isolated. A 0.5 g portion of the kidney was homogenized with 1 ml of distilled water (using a Polytron homogenizer) and centrifuged at 13000 rpm (4° C.) for 10 minutes. The supernatant was taken and used as a sample. This sample was diluted 20-fold with a buffer solution and 0.3 μl portion of this sample was applied to a cellulose acetate membrane and using 0.1M Tris-sodium hydrogen phosphate buffer (pH 8.1), electrophoresis in the direction of − to + was performed at 4° C. and 200 V for 90 minutes.

After electrophoresis, the Fh-1 was stained using the dye bath described below and fixed with 5% acetic acid and the type of Fh-1 in the sample was determined from the migration distance in accordance with the literature [Carleer, J. and Ansay, M., Int. J. Biochem., 7, 565–566 (1976); Cramer, D. V., Blankert, J. J. and Paul, L. C., Biochem. Genet., 23, 623–629 (1985)].

[Dye bath composition]

Fumaric acid 6 mg

NAD (25 mg/ml) 0.08 ml

Sodium pyruvate (50 mg/ml) 0.04 ml

MTT (6 mg/ml) 0.08 ml

PMS (2 mg/ml) 0.25 ml 0.2M Tris-HCl buffer (pH 8.0) 2 ml

Malate dehydrogenase 60 IU

DW To make 1000 ml

(17) Typing of plasma group-specific component (GC)

A rat was laparotomized under ether anesthesia and the blood was drawn from the abdominal inferior vena cava. The collected blood was centrifuged at 3000 rpm (40° C.) for 10 minutes to separate the plasma.

The plasma was diluted 2-fold with the diluent IVA and a 5 μl portion of the dilution was applied to the same 10% polyacrylamide gel as used under (5)–(9). Then, using 0.0125M Tris-glycine buffer (pH 6.8), electrophoresis in the direction of − to + was performed at 4° C. and 15 mA for 65 minutes.

After electrophoresis, the GC was stained with Ponceau-S (Helena) and treated with 5% acetic acid for bleaching and fixation and the type of GC in the above sample was determined from the migration distance in accordance with the literature [Moutier, R., Biochem. Genet., 8, 321–328 (1973)].

(18) Typing of liver glycerophosphate dehydrogenase-1 (Gdc-1)

The typing of Gdc-1 was performed in accordance with Eriksson's method [Eriksson, K., Heredity., 37, 341–349 (1976)].

Thus, 0.5 g of liver tissue was homogenized with 1 ml of distilled water (using a Polytron homogenizer) and centrifuged at 13000 rpm (4° C.) for 10 minutes. The supernatant was taken and used. To one volume of the supernatant was added one volume of a sample buffer [0.037 g of EDTA 2Na and 10 μl of 2-mercaptoethanol added to 100 ml of 0.0068M Tris-0.0011M citric acid] to prepare a sample. A 0.6 μl portion of this sample was applied to a cellulose acetate membrane (Titan III-Lipo, Helena) and using 0.137M Tris-0.02M citric acid buffer (pH 8.3), electrophoresis in the direction of − to + was performed at 180 V (10° C) for 75 minutes.

After electrophoresis, the cellulose acetate membrane was stained with the dye solution described below (37° C., 30 minutes) and fixed with 5% acetic acid. The type of Gdc-1 in the sample was then determined from the migration distance in accordance with the literature referred to above.

[Dye bath composition]:

0.2M Tris-HCl (pH 9.0) 1.6 ml

PMS (2.4 mg/ml) 0.2 ml

MTT (10 mg/ml) 0.2 ml

NAD (50 mg/ml) 0.4 ml

DL-α-Glycerophosphate (100 mg/ml) 0.1 ml

Sodium pyruvate 20 mg

DW To make 10 ml

(19) Typing of liver hydroxy-acid oxidase-1 (Hao-1)

The typing of Hao-1 was performed in accordance with Cramer's method [Cramer, D. V., Biochem. Genet., 24, 217–227 (1986)]. Thus, 0.5 g of liver tissue was homogenized with 1 ml of distilled water (using a Polytron homogenizer) and centrifuged at 13000 rpm (4° C.) for 10 minutes. The supernatant was taken and used as a sample.

A 0.9 μl portion of the above sample was applied to a cellulose acetate membrane (Titan III-Lipo, Helena) and using Tris-citric acid buffer (0.034M Tris–0.005M citric acid, pH 8.3), electrophoresis in the direction of − to + was performed at 200 V (4° C.) for 30 minutes.

After electrophoresis, the cellulose acetate membrane was stained with the dye solution described below (37° C., 30 minutes) and fixed with 5% acetic acid. The type of Hao-1 in the sample was then determined from the migration pattern in accordance with the literature referred to above.

|Dye bath composition|

1M Tris-HCl (pH 7.4) 0.02 ml

DL-α-Hydroxyisocaproic acid 13 mg o-Dianisidine 5 mg

Peroxidase 1 mg

DW To make 10 ml

(20) Typing of erythrocyte hemoglobin β-chain (Hbb)

A rat was laparotomized under ether anesthesia and the blood was drawn from the abdominal inferior vena cava. The collected blood was centrifuged at 3000 rpm (4° C.) for 10 minutes and the erythrocytes were washed by adding 5 ml of 0.85% NaCl solution. This washing procedure was performed twice, followed by centrifuging under the above conditions to provide an erythrocyte pack (RBC pack). To one volume of this RBC pack was added four volumes of Tris-borate buffer (0.065M Tris, 0.024M boric acid, pH 9.0) for hemolysis and the mixture was centrifuged at 13000 rpm (4° C.) for 10 minutes. Then, using the supernatant, typing of Hbb was performed in accordance with the literature [Brdicka, R., Folia Biologica (Prague), 11, 328–329 (1965)].

The above sample was applied, in a portion of 0.3 μl, to a cellulose acetate membrane (Helena). Then, using Tris-borate buffer (pH 8.4) containing 0.0016M EDTA-2Na, electrophoresis in the direction of − to + was then performed at 350 V for 30 minutes (4° C.).

After electrophoresis, the Hbb was stained with Ponceau-S (Helena) and treated with 5% acetic acid for bleaching and fixation and the type of Hbb in the above sample was determined from the migration distance in accordance with the literature mentioned above.

(21) Typing of digestive tract mucosal urinary pepsi nogen-1 (Pg-1)

A rat was laparotomized under ether anesthesia and the gastric mucosa was taken out. A 0.5 g portion of the mucosal tissue was homogenized with 1 ml of distilled water (using a Polytron homogenizer) and centrifuged at 13000 rpm (4° C.) for 10 minutes. The super natant was taken and used as a sample.

This sample was diluted four-fold with the diluent IVA and a 10 μl portion of this sample was applied to the same 10% polyacrylamide gel as used under (5)–(9) and using Tris-glycine buffer (pH 8.6), electrophoresis in the direction of − to + was performed at 10 mA for 30 minutes and, then, at 15 mA for 25 minutes (4° C.).

After electrophoresis, the sample was saturated with 100 ml of 0.1 N-HCl containing 0.7 g of bovine hemoglobin for 15 minutes and, then, further saturated with 0.1 N-HCl for 60 minutes. Thereafter, the sample was stained with 0.05% Coomassie brilliant blue (containing 30% methanol and 10% acetone) and bleached with 30% methanol-10% acetone. The type of Pg-1 in the sample was determined from the migration distance in accordance with the literature [Cramer, D. V., Immunogenet., 13, 555–558 (1981)]

(22) Typing of phosphogluconate dehydrogenase (Pgd)

A rat was laparotomized under ether anesthesia and the kidneys were isolated. A 0.5 g portion of the kidney was homogenized with 1 ml of distilled water (using a Polytron homogenizer) and centrifuged at 13000 rpm (4° C.) for 10 minutes. The supernatant was taken and used as a sample. A 0.6 μl portion of this sample was applied to a cellulose acetate membrane (Lipo, Helena) and using 0.5M phosphate buffer (pH 7.0), electrophoresis in the direction of − to + was performed at 200 V (4° C.) for 30 minutes. After electrophoresis, the Pgd was stained using the dye bath described below and fixed with 5% acetic acid and the type of Pgd in the sample was determined from the migration distance in accordance with the literature [Carter, N. D., Nature, 224, 1214 (1969)].

|Dye bath composition|

1M Tris-HCl (pH 8.0) 1 ml

6-Phospho-D-gluconic acid trisodium salt (1 mg/5 μl) 10 μl

1M Magnesium chloride 1 ml

Nicotinamide adenine dinucleotide phosphate (NADP) 1 mg 3-(4,5-Dimethylthiazolyl)-2,5-diphenyltetrazolium bromide (MTT) 1 mg DW To make 10 ml

(23) Typing of seminal vesicle protein (Svp-1)

A rat was laparotomized under ether anesthesia and the seminal vesicle was removed. The gonecyst fluid was squeezed out into 1 ml of distilled water and, after thorough shaking, centrifuged at 13000 rpm (4° C.) for 10 minutes. The supernatant was taken and used as a sample. A 0.6 μl portion of this sample was applied to a cellulose acetate membrane (Helena) and electrophoresis in the direction of − to + was performed at 400 V (4° C.) for 30 minutes.

After electrophoresis, the Svp-1 was stained with Ponceau-S (Helena) and treated with 5% acetic acid for bleaching and fixation and the type of Svp-1 in the above sample was determined from the migration distance in accordance with the literature [Gasser, D. L., Biochem. Genet., 6, 61–63 (1972)].

The allelic distributions of the non-insulin dependent diabetic rat (OLETF) of the invention and the control rat (LETO) are shown below in Table 1.

TABLE 1

| Symbol | Linkage group | Tissue | OLETF | LETO |
| --- | --- | --- | --- | --- |
| Acp-2 | — | Testis | a | a |
| Ahd-2 | — | Liver | c | c |
| Ahd-c | X | Liver | a | a |
| Cs-1 | II | Red blood cell | b | b |
| Es-1 | V | Small intestine | b | b |
| Es-1 | V | Plasma | b | b |
| Es-2 | V | Plasma | d | a |
| Es-3 | V | Small intestine | c | a |
| Es-4 | V | Kidney | b | b |
| Es-6 | — | Testis | a | a |
| Es-7 | V | Lung | b | b |
| Es-8 | V | Testis | a | b |
| Es-9 | V | Testis | c | a |
| Es-10 | V | Testis | b | a |
| Es-Si | V | Plasma | a | a |
| Fh-1 | X | Kidney | b | b |
| GC | VI | Plasma | b | b |
| Gdc-1 | — | Liver | a | a |
| Hao-1 | IV | Liver | a | a |
| Hbb | I | Red blood cell | b | b |
| Pg-1 | — | Gastric mucosa | a | a |
| Pgd | — | Kidney | b | b |
| Svp-1 | IV | Seminal vesicle | a | a |

EXAMPLE 5

Typing of major histocompatibility antigen (RT-1)

(1) Typing of RT-1 class I antigen on the erythrocyte

A small quantity of blood was drawn from the tail vein of a rat, and 15 ml of a solution containing 0.01M EDTA in 0.15M NaCl+0.02M HEPES (pH 7.2) was taken in a centrifuge tube. Then, 300 µl of the above blood was placed thereon and immediately covered with a parafin film, followed by shaking. This was then centrifuged at 1000 rpm for 10 minutes for washing. The sediment was serially washed with 3 portions of the above buffer free of EDTA and centrifuged for a third time at 2000 rpm for 10 minutes to obtain a blood cell pack.

Then, the washed blood was added to a solution containing one volume of Dextran 70 (average MW=70000, 6 w/v % glucose, Dextran D "Otsuka"), 4 volumes of 0.15M NaCl +0.02M HEPES (pH 7.2) and a final concentration of 1% of FCS to prepare a 1% erythrocyte suspension.

The above buffer containing both dextran and FCS was placed, in 25 µl portions, in the wells of a disposable U plate (Sanko Pure Chemicals). Then, the antiserum previously diluted 5- or 10-fold was gradually diluted and distributed into the wells. Following addition of 25 µl of the 1% erythrocyte suspension, the plate was shaken on a micro-mixer (Taiyo Scientific Industry) and allowed to stand at 37° C. for 1 hour.

The antiserum mentioned above w as the anti-W/Ms antibody to the inbred rat F344/Ms which was maintained at National Institute of Genetics (Ms). As to the RT-1class I antigen of the above inbred rat, its typing has already been carried out and the F344 used above is classified as 1 on the panel of antiserum and W/Ms as 2 on the panel of antiserum. The above type 1 is discriminated alphabetically as 1, type 2 as u, type 3 as n and type 4 as a. An antiserum with anti-u antibody is prepared by immunizing F344/Ms with the splenic cells of W/Ms and when th is anti-u antibody is absorbed with a type u rat, its titer is lost. Thus, when absorption is made with the red blood cells of W/Ms, complete loss of titer occurs.

(2) Typing of RT-1 class II antigen on the B lymphocyte

The lymph node was excised from a rat under ether anesthesia and loosened with pincers in RPMI 1640 medium (Nissui Pharmaceutical) containing 10% FCS to give a suspension of lymphocytes. This lymphocyte suspension was placed in a nylon wool column (Sanko Pure Chemicals) and allowed to stand at 37° C. for 60 minutes. Then, 10 ml of the above medium was passed through the nylon wool column to wash out the T-lymphocytes. The nylon wool was then taken out and pressed with fingers to liberate the adhered B-lymphocytes and using FCS-free RPMI 1640, a suspension of 1×10⁶ cells/ml was prepared. The B-cell suspension was distributed in 1 µl portions into an acrylic resin plate (Ishikawa Seisakusho) and the antiserum diluted beforehand was placed in 1 µl portions. Finally, 1 µl portions of rabbit serum as the complement were added and the plate was allowed to stand at 37° C. for 60 minutes. Then, a 2% solution of glutaraldehyde (Naka lai Tesque) containing 20% of glycerin (Wako Pure Chemicals) was added for fixation and the viability of cells was examined with a phase-contrast microscope (Olympus).

As the above antiserum, the TO antibody to W/Hok, the SDJ antibody to F344 and the F344 antibody to ACI were used. Since SDJ rats and WF rats for which the typing of the RT-1 class II antigen on the B-lymphocytes has already been carried out react with the above-mentioned three antibodies, the RT-1 class II antigen has been classified as u. As the OLETF rat also reacts with these same antibodies, the RT-1 class II antigen on the B-lymphocyte was classified as u.

The results of typing for class I and class II of the above major histocompatibility antigen (RT-1) are shown below in Table 2.

TABLE 2

| Major histocompatibility antigen (RT-1) | Type |
|---|---|
| Class I antigen on erythrocyte | u |
| Class II antigen on B-lymphocyte | u |

The result of RT-1 determination in the OLETF rat of the invention was identical with that in the control rat (LETO).

A deposit of OLETF rat embryos was made with the ATCC, 12301 Parklawn Dr., Rockville, Md. 20852, USA on Aug. 24, 1994 with accession number ATCC 72016.

We claim:

1. A non-insulin-dependent diabetic mellitus male rat obtained by selective breeding of Long-Evans rats, wherein said male rat spontaneously develops non-insulin-dependent diabetic mellitus, and wherein said rat strain develops polyuria, polyphagia, polydispia, degeneration of pancreatic islet cells, glomeruli lesions, nodules and obesity.

2. The non-insulin-dependent diabetic mellitus rat as claimed in claim 1 whose biochemical gene markers in the organs, plasma and red blood cells respectively specified below are of the following types:

| Biochemical gene locus | Type |
|---|---|
| Testicle acid phosphatase 2 | a |
| Testicle esterase 6 | a |
| Lung esterase 7 | b |
| Testicle esterase 8 | a |
| Testicle esterase 9 | c |
| Testicle esterase 10 | b |
| Liver aldehyde dehydrogenase 2 | c |
| Liver aldehyde dehydrogenase c | a |
| Liver glycerophosphate dehydrogenase 1 | a |
| Liver hydroxy acid oxidase | a |
| Erythrocyte catalase 1 | b |
| Erythrocyte hemoglobin beta chain | b |
| Plasma esterase 1 | b |
| Plasma esterase 2 | d |
| Plasma esterase Si | a |
| Plasma group-specific component | b |
| Small intestine esterase 1 | b |
| Small intestine esterase 3 | c |
| Digestive tract mucosa urinary pepsinogen 1 | a |
| Kidney esterase 4 | b |
| Kidney fumarate hydrogenase 1 | b |
| Kidney phosphogluconate dehydrogenase | b |
| Seminal vesticle protein 1 | a |

3. The non-insulin-dependent diabetic mellitus rat as claimed in claim 1 whose erythrocytes and B lymphocytes have the following major histocompatibility antigen (RT1) markers:

| Major histocompatibility antigen (RT1) | Type |
|---|---|
| Erythrocyte RT1 class I antigen | u |
| B lymphocyte RT1 class II antigen | u |

4. The non-insulin dependent diabetic mellitus rat as claim in claim 1 wherein an oral glucose tolerance test demonstrates increases in plasma glucose and insulin levels when compared to non-diabetic rats, and wherein the urinary protein level increases with age when compared to non-diabetic rats.

* * * * *